United States Patent
Ben David et al.

(10) Patent No.: US 11,129,540 B2
(45) Date of Patent: Sep. 28, 2021

(54) DEVICE, SYSTEM AND METHOD FOR MONITORING A SURGICAL SITE

(71) Applicant: MOR RESEARCH APPLICATIONS LTD, Tel Aviv (IL)

(72) Inventors: Matan Ben David, Tel Aviv (IL); Amir Kraitzer, Hertzelia (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 455 days.

(21) Appl. No.: 15/744,083

(22) PCT Filed: Jul. 14, 2016

(86) PCT No.: PCT/IL2016/050771
§ 371 (c)(1),
(2) Date: Jan. 12, 2018

(87) PCT Pub. No.: WO2017/009849
PCT Pub. Date: Jan. 19, 2017

(65) Prior Publication Data
US 2018/0206754 A1    Jul. 26, 2018

Related U.S. Application Data

(60) Provisional application No. 62/192,395, filed on Jul. 14, 2015.

(51) Int. Cl.
*A61B 5/00* (2006.01)
*A61B 5/053* (2021.01)
(Continued)

(52) U.S. Cl.
CPC ............ *A61B 5/053* (2013.01); *A61B 5/0538* (2013.01); *A61B 5/4842* (2013.01);
(Continued)

(58) Field of Classification Search
CPC . A61B 5/6833; A61B 2217/005; A61B 5/686; A61B 2017/00004; A61B 2018/00648; A61B 5/14539
(Continued)

(56) References Cited

U.S. PATENT DOCUMENTS 7,899,508 B2    3/2011  Dearmond
8,070,807 B2 *  12/2011  Chen .................. A61F 2/12
                                          600/301
(Continued)

FOREIGN PATENT DOCUMENTS

CN      203591517 U     5/2014
DE      102013200806 A1  7/2014
(Continued)

OTHER PUBLICATIONS

International Search Report of PCT/IB2019/056247 dated Nov. 14, 2019.
(Continued)

*Primary Examiner* — May A Abouelela
(74) *Attorney, Agent, or Firm* — Browdy and Neimark, PLLC

(57) ABSTRACT

Embodiments relate to an implantable device for detecting leakage of matter from a mammalian lumen, the device comprising a mesh structure that is attachable to a lumen of a mammalian. The mesh structure comprises a material or a material composition that is electrically conductive and which is measurably responsive in terms of its electrical conductivity when being subjected to leakage of matter from the lumen.

20 Claims, 4 Drawing Sheets

(51) Int. Cl.
  *A61B 5/0538* (2021.01)
  *A61B 17/11* (2006.01)
  *A61B 17/00* (2006.01)
  *A61B 5/145* (2006.01)
(52) U.S. Cl.
  CPC ............ *A61B 5/4851* (2013.01); *A61B 5/686* (2013.01); *A61B 5/6871* (2013.01); *A61B 5/6873* (2013.01); *A61B 17/1114* (2013.01); *A61B 5/14539* (2013.01); *A61B 2017/0003* (2013.01); *A61B 2017/00004* (2013.01); *A61B 2017/00022* (2013.01); *A61B 2017/00035* (2013.01); *A61B 2017/00199* (2013.01); *A61B 2017/1132* (2013.01)
(58) Field of Classification Search
  USPC .................. 600/302, 372, 547; 606/151, 154
  See application file for complete search history.

(56) References Cited

U.S. PATENT DOCUMENTS

| | | | |
|---|---|---|---|
| 8,118,206 | B2 | 2/2012 | Sand et al. |
| 8,267,888 | B2* | 9/2012 | Marco ..................... A61F 5/003 604/104 |
| 8,297,108 | B2 | 10/2012 | Abboud et al. |
| 2002/0111544 | A1 | 8/2002 | Iddan |
| 2005/0240093 | A1 | 10/2005 | Dearmond |
| 2006/0111777 | A1* | 5/2006 | Chen ........................ A61F 2/12 623/8 |
| 2007/0224244 | A1 | 9/2007 | Weber et al. |
| 2008/0262613 | A1* | 10/2008 | Gogolewski ....... C08G 18/3203 623/11.11 |
| 2009/0259301 | A1 | 10/2009 | Gelbart |
| 2010/0010519 | A1* | 1/2010 | Stopek ................... A61B 17/11 606/154 |
| 2010/0094316 | A1* | 4/2010 | Rupp ............. A61B 17/320016 606/151 |
| 2011/0077476 | A1* | 3/2011 | Rofougaran ........ G06F 19/3418 600/302 |
| 2012/0273548 | A1 | 11/2012 | Ma et al. |
| 2013/0018235 | A1* | 1/2013 | Thompson ........... A61B 5/0002 600/302 |
| 2013/0150685 | A1 | 6/2013 | Toth |
| 2013/0289367 | A1 | 10/2013 | Kruglick |
| 2014/0018696 | A1 | 1/2014 | Dearmond |
| 2014/0066959 | A1* | 3/2014 | Bonutti ................... A61L 27/12 606/151 |
| 2015/0018855 | A1* | 1/2015 | Borkar ................. A61B 5/4851 606/154 |
| 2015/0238300 | A1* | 8/2015 | Wang ..................... A61F 2/0063 606/151 |
| 2015/0289929 | A1* | 10/2015 | Toth ................... A61B 18/1492 600/372 |
| 2016/0029921 | A1* | 2/2016 | Pradhan ............. A61B 5/14507 600/302 |
| 2017/0020402 | A1 | 1/2017 | Rogers et al. |
| 2018/0206754 | A1 | 7/2018 | Ben David |

FOREIGN PATENT DOCUMENTS

| | | |
|---|---|---|
| WO | 2008005388 A2 | 1/2008 |
| WO | 2010099321 | 9/2010 |
| WO | 2010099321 A1 | 9/2010 |
| WO | 2012145548 | 10/2012 |
| WO | 2012145548 A2 | 10/2012 |
| WO | 2014007821 A1 | 4/2014 |
| WO | 2014052908 A1 | 4/2014 |
| WO | 2014055521 A1 | 4/2014 |
| WO | 2014074105 A1 | 5/2014 |
| WO | 2014163983 A1 | 10/2014 |
| WO | 2018140693 A1 | 8/2018 |
| WO | 2017009849 A1 | 1/2019 |

OTHER PUBLICATIONS

Written Opinion of PCT/IB2019/056247 dated Nov. 14, 2019.
Israel Search Strategy Report of PCT/IB2019/056247 dated Nov. 12, 2019.
Richard Balint et al., "Conductive polymers: Towards a smart biomaterial for tissue Engineering", Acta Biomaterialia 10 (2014) pp. 2341-2353.
Daniel DeArmond et al., "Anastomotic Leak Detection by Electrolyte Electrical Resistance", Journal of Investigative Surgery; 23, pp. 197-203, (2010).
Julie Kim et al., "ASMBS position statement on prevention, detection, and treatment of gastrointestinal leak after gastric bypass and sleeve gastrectomy, including the roles of imaging, surgical exploration, and nonoperative management", Surgery for Obesity arid Related Diseases; (2015) 00-00.
Maryam Moravej et al., Biodegradable Metals for Cardiovascular Stent Application: Interests and New Opportunities; Int. J. Mol. Sci. (2011), 12, 4250-4270; doi:10.3390/ijms12074250.
Freek Daams et ai., Prediction and diagnosis of colorectal anastomotic leakage: A systematic review of literature; World J Gastrointest Surg Feb. 27, 2014; 6(2): 14-26.
C. Cini et al., Peritoneal fluid cytokines and matrix metalloproteinases as early markers of anastomotic leakage in colorectal anastomosis: a literature review and meta-analysis; doi:10.1111/codi.12192; Received Apr. 24, 2012; accepted Nov. 4, 2012; Accepted Article online Mar. 5, 2013.
Extended European Search Report for EP16823995 dated Mar. 1, 2019.
Office Action issued by the China National Intellectual Property Administration (CNIPA) for Chinese Patent Application No. 201680046642.2 dated Jan. 3, 2020 with English translation.
"2nd CN office action dated Oct. 14, 2020 regarding application CN201680046642.2 (original & Google-based machine translation)".
"3rd Chinese Office Action dated Mar. 3, 2021, regarding CN201680046642.2 (original & Google-based machine translation)".
International Preliminary Report on Patentability for Application No. PCT/IL2016/050771, dated Jan. 16, 2018, 5 pages.
International Search Report and Written Opinion for Application No. PCT/IL2016/050771, dated Nov. 3, 2016, 7 pages.
Clémentine M. Boutry et al. "Towards biodegradable wireless implants", Phil. Trans. R. Soc. A 370, 2418-2432, doi:10.1098/rsta.2011.0439.
Jonathan Rigelsford et al. "Passive Biodegradable Implant for Subcutaneous Soft-Tissue Trauma Monitoring", IEEE Journal of Biomedical and Health Informatics, vol. 00, No. 00, 00 2015, DOI 10.1109/JBHI.2015.2417754.

* cited by examiner

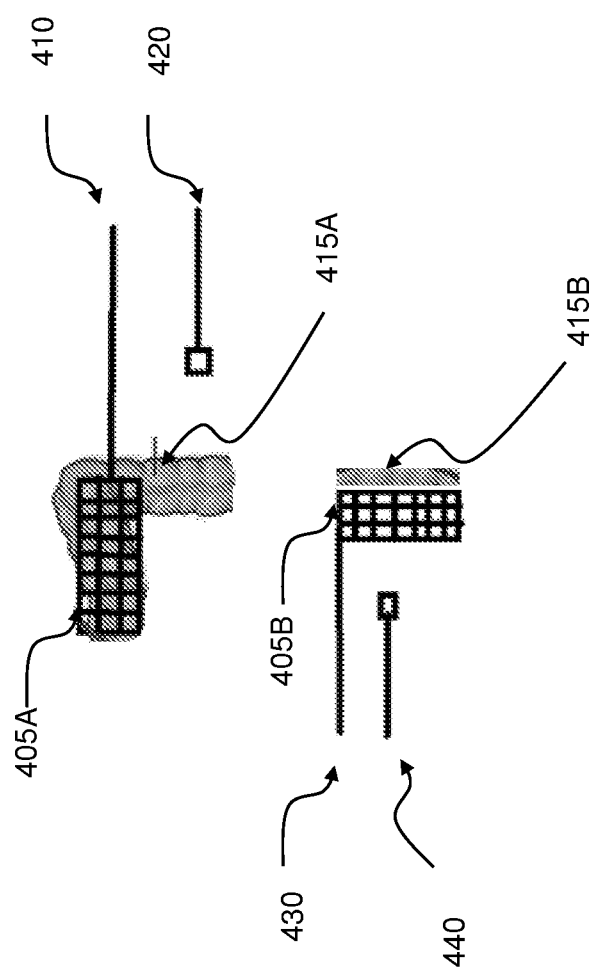

DEVICE, SYSTEM AND METHOD FOR MONITORING A SURGICAL SITE

This application claims the benefit of priority from U.S. Provisional Patent Application No. 62/192,395, filed on Jul. 14, 2015. The content of the above document is incorporated by reference in its entirety as if fully set forth herein.

FIELD

Embodiments disclosed herein relate in general to the detection of leakage from the gastrointestinal system.

BACKGROUND

Various surgical procedures involve removal of a tissue section from the gastrointestinal tract. The removal of a tissue section is followed by re-connecting the remaining tissue portions as in Bariatric surgery or by reconnecting a first tubular tissue portion with another tubular tissue portion, also known as anastomosis, to re-establish tissue continuity of the gastrointestinal tract. The reconnection of tissue portions can be performed using surgical staplers or suturing material. The quality of such tissue reconnection and thus the occurrence of leaks is, in general, not surgeon dependent.

As is well known, the presence of leaks at sites where gastrointestinal tissue portions were reconnected can result in significant health problems and be potentially devastating. Early diagnosis of the presence of leaks in a post-surgical setting is thus of paramount importance to minimize morbidity and mortality rates. However, as these sites are internal to the body, early detection is difficult and/or costly.

The description above is presented as a general overview of related art in this field and should not be construed as an admission that any of the information it contains constitutes prior art against the present patent application.

SUMMARY

Aspects of disclosed embodiments relate to an implantable device for monitoring a site of biological tissue like, e.g., a surgical site inside a living body of, e.g., mammalian body such as without limitation, a human body, for example, to detect leakage of body matter (e.g., body fluid) from an organ inside the body Accordingly, such device may be employed for monitoring the integrity of an organ, for example, for detecting leakage of body fluid from a lumen or cavity of the organ.

According to example 1, the device comprises a wire or a mesh structure that is positionable around an organ (e.g., around a lumen) of a mammalian body. The mesh structure comprises a material or a material composition that is electrically conductive and which is measurably responsive in terms of its electrical conductivity when being subjected to leakage of body matter from the body organ.

Example 2 includes the subject matter of example 1 and, optionally, allows direct measurement of changes of an electrical property of biological tissue of the body organ.

Example 3 includes the subject matter of examples 1 or 2 and, optionally, wherein the body organ is any one of: the stomach, the small intestine, the large intestine and/or the esophagus.

Example 4 includes the subject matter of any of the examples 1 to 3 and, optionally, wherein the mesh structure comprises conductive material and biocompatible and, further optionally, biodegradable material.

Example 5 includes the subject matter of example 4 and, optionally, wherein the biodegradable conductive material is a biodegradable conductive polymer and/or a biodegradable conductive metal.

Example 6 includes the subject matter of example 4 and, optionally, wherein the biodegradable polymer comprises Polypyrrole or any derivatives thereof.

Example 7 includes the subject matter of example 4 and, optionally, wherein the biodegradable conductive metal comprises magnesium, or a combination thereof.

Example 8 includes a system for monitoring a site within a mammalian body, comprising an implantable device according to any of the examples 1 to 7 and which is configured to be operably attachable to an organ inside the mammalian body; and a leak monitoring device which is operably coupled with the implant and which comprises: a power source for delivering electrical energy to the implant; and a detector engine for measuring changes in the electrical properties of the implantable device.

According to an aspect of some embodiments of the present invention, there is provided an implantable device comprising at least two wires, wherein at least one wire is configured to attach along a site of an organ, and wherein the at least one wire comprises a biodegradable conductive polymer and/or a biodegradable conductive metal.

In some embodiments, the implantable device is for monitoring biological tissue leakage of body matter from an organ (e.g., a body organ or a lumen thereof) of a mammalian body.

In some embodiments, the at least two wires are in the form of mesh structure.

In some embodiments, at least one wire is positioned external to the body organ.

In some embodiments, the biodegradable conductive metal comprises a metal selected from the group consisting of magnesium, iron, zinc and calcium, or any combination thereof.

In some embodiments, the body organ is the stomach, the small intestine, or the large intestine.

In some embodiments, the biodegradable conductive polymer or the biodegradable conductive metal is characterized as being measurably responsive in terms of its electrical conductivity when being subjected to body matter leaking from the body organ.

In some embodiments, the body matter is a cytokine or an enzyme.

In some embodiments, the enzyme is metalloproteinase.

In some embodiments, the metalloproteinase is selected from the group consisting of MMP-8 and MMP-9.

In some embodiments, the body matter is characterized by a pH value that varies within ±0.5.

In some embodiments, the biodegradable conductive polymer or the biodegradable conductive metal is characterized by a conductivity (S/cm) having a value of 100 to 7,500 S/cm.

According to an aspect of some embodiments of the present invention, there is provided a system for monitoring a site within a mammalian body, comprising an implantable device according to any of the preceding claims which is configured to be operably attachable to an organ inside the mammalian body; and a leak monitoring device which is operably coupled with the implant and which comprises a power source for delivering electrical energy to the implant; and a detector engine for measuring changes in the electrical properties of the implantable device.

According to an aspect of some embodiments of the present invention, there is provided a method comprising attaching at least one wire along a site of an organ, wherein the at least one wire is configured to attach to along a site of an organ, and wherein the at least one wire comprises a biodegradable conductive polymer and/or a biodegradable conductive metal, the method further comprising monitoring biological tissue leakage of body matter from a body organ.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE FIGURES

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

FIG. 4 schematically illustrates the implantable device of FIG. 2A where the implantable device is implanted in the colon, according to an embodiment.

DETAILED DESCRIPTION OF EMBODIMENTS

The description is given with reference to particular examples, with the understanding that such device, system and method are not limited to these examples.

Aspects of embodiments disclosed in this description relate to a device, system and method for monitoring the integrity of an organ inside a body, e.g., to detect leakage of body matter from the organ (e.g., the gastrointestinal or GI tract). Such leakage may include post-operative leakage.

In some embodiments, the device has at least two wires.

In some embodiments, at least one wire is configured to attach along a site of an organ.

In some embodiments, at least wire comprises a biodegradable conductive polymer and/or a biodegradable conductive metal.

Non-limiting examples of the organ may include any one of the following: the stomach, the small intestine, the large intestine, the esophagus, and/or any other, for example, hollow tubular organ.

It is further noted that the term "detection" as well as grammatical variations thereof may encompass any processes that enable such "detection", including sensing and/or monitoring.

Figure 1:
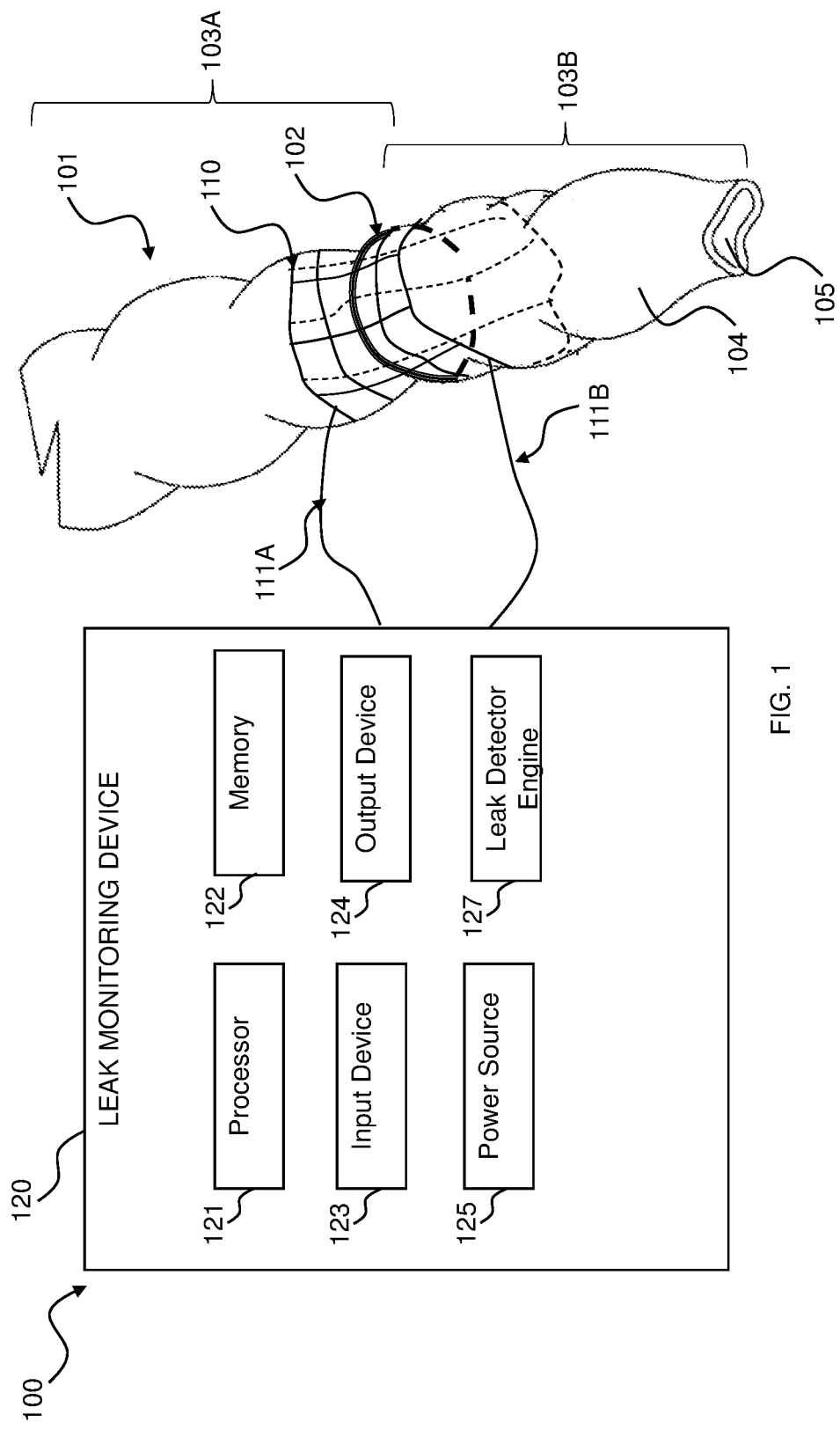
FIG. 1 schematically illustrates a system for the monitoring of a surgical site of a body organ, according to an embodiment.

Reference is made to FIG. 1. Generally, a system 100 for monitoring an organ 101 inside the body, e.g., for detecting leakage of body matter from organ 101 through reconnection site 102 at which a first and second tubular tissue portion 103B and 103A of the organ were reconnected in a surgical procedure, comprises an implantable device 110 and a leak monitoring device 120 operatively coupled with implantable device 110.

The term "operatively coupled" may encompass the meanings of the terms "responsively coupled", "communicably coupled", and the like.

In an embodiment, implantable device 110 may have electrical properties (e.g., conductivity) allowing the device to be employed to monitor changes in an environment occurring at and/or in the vicinity of reconnection site 102.

Such environmental change might be indicative of leakage of matter from the organ of, e.g., gastrointestinal (GI) tract 101 through reconnection site 102 to the outside of the tract or organ, and may for example include a decrease or increase in pH value, increase in lactate concentration and/or enzymatic activity, which may for example result in an increase to the implantable device's exposure to inflammatory response, e.g., increase of matrix metalloproteinase enzymes (MMP), interleukin (IL)-6, and/or any other change(s) in an environmental parameter as further described below. Accordingly, implantable device 110 exposed to such environmental changes when being set in an operable position (for example, topically, e.g., when engaging a biological tissue region to overlay a reconnection site) may allow detection of leakage of body matter from organ 101.

In some embodiments, the term "gastrointestinal tract", as used herein, is defined as the part of the body which includes the esophagus, stomach and small and large intestines. In some embodiments, the term "topical", or any grammatical variation thereof, is defined as application to the mucosal surfaces of the body and include applications to areas of the gastrointestinal tract.

In some embodiments, the term "metalloproteinase", or "metalloprotease", as used herein, may refer to protease enzyme whose catalytic mechanism may involve a metal.

The term "metalloproteinases" includes, but is not limited to, the collagenases, gelatinases, stromelysins, matrilysin (MMP-7); enamelysin (MMP-20), macrophage metalloelastase (MMP12), MMP-19 and membrane-type metalloproteinases (MT-MMP-1 to 4, stromelysin-3, and MMP-11).

Environmental changes at reconnection site 102 may cause changes to the biological tissue to which implantable device 110 is attached and, as a result thereof, correspondingly impact the electrical properties of the tissue.

According to an embodiment, changes in an electrical property of biological tissue may be read out and monitored by leak monitoring device 120 via implantable device 110 covering a region of the impacted biological tissue, as outlined in the following.

For instance, implantable device 110 may exhibit at least one electrical property which is responsive to body matter or overall inflammatory response that may flow and/or be stored, e.g., in GI tract 101 or in any other organ and which is measurable by leak monitoring device 120. For example, implantable device 110 may comprise material or materials that are electrically conductive and responsive to body matter that is known to be flowing within the lumen of a body organ 101 (e.g. GI tract). For example, implantable device 110 may undergo structural change(s) when being subjected to or engaging with body matter. These structural changes may, for example, include at least partial or full material degradation comprised in implantable device 110. Responsive to such structural changes, the electrical properties of implantable device 110 may be altered. Changes in the electrical properties of implantable device 110 may be measured by leak monitoring device 120 using, e.g., DC or AC current. Such readout or measurement of environmental changes may herein be referred to as "indirect measurement".

In some embodiments, the electric property refers to current density. In some embodiments, the current density is calculated from electrode potential curve(s), i.e. polarization curve(s).

In some embodiments, from such curves it is possible to calculate the number of ions per unit time liberated into the tissue as well as the depth of the metal removed by corrosion for a given time (referred to as "corrosion rate").

As further described hereinbelow, the corrosion rate can be calculated and compared with an electrode that is placed outside the region suspected to undergo an environmental change, due to e.g., inflammation. The higher the current difference between the electrodes, the higher the chance that inflammation has caused more pronounced degradation and thus may predict leakage.

In some embodiments, implantable device 110 has a biodegradable portion and an unchanged portion (also referred to herein as: "reference portion"). In some embodiments, the unchanged portion is used to provide a common reference from which structural changes can be measured and/or calculated. That is, in some embodiments, the measurement refers to changes in the structure profile of the biodegradable portion.

In some embodiments, the changes measured in the structure profile are calculated without reference to an area of unchanged topography.

The reference portion may be implanted in the body.

The reference portion and the biodegradable portion may be both located within the same organ.

The reference may be implanted outside the body. The reference portion may comprise a metal coated with a polymer.

In some embodiments, detection of leakage is performed by a sequence of individual measurements. In some embodiments, the results of several measurements are stored in logic circuit until a desired number of "n" of individual measurements have been accumulated, whereupon an average measured or test value is formed.

Direct measurement may relate to measuring changes of an electrical property of biological tissue of an organ, e.g., by operably positioning at least two electrodes (not shown) distantly from one another for allowing electrical DC or AC current to flow from one electrode to the other electrode via the biological tissue.

To simplify the discussion that follows, the monitoring of the integrity of an organ may herein be construed as to comprise indirect and, optionally, direct measurement of the electrical properties of biological tissue.

An electrical property (whether acquired through direct or indirect measurement) may for example comprise impedance, conductivity, electric potential difference, capacitance, or any other suitable parameter. An electrical property may be measured as function of time.

A change in the electrical property as measured by leak monitoring device 120 via implantable device 110 may be indicative of leakage from organ 101. For example, if the measured impedance of implantable device 110 is above or below an impedance threshold value for a certain period of time, it may be inferred that leakage is occurring.

While the discussion that follows relates to the detection of leakage through tissue reconnection site 102 connecting between tubular tissue portions 103A and 103B, also known as "Anastomosis", this should by no means to be construed as limiting. The system, device and method disclosed herein is thus not only suitable to detect anastomotic leakage but also leakage which may be the result of a surgical procedure including, for example, Bariatric surgeries like, e.g., sleeve gastrectomy; and/or esophagectomy (for generating a gastric conduit by the stomach in place of the esophagus).

Reconnection site 102 comprises tissues of either tissue portions 103A and 103B and a surgical tissue connector assembly for securing opposing ends of tissue portions 103A and 103B in a position to bring them in fluid communication with each other such to re-establish tissue continuity of the mammalian body organ. Such connector assembly may comprise, for example, surgical staples and/or one or more suture threads.

Implantable device 110 may have a wire-like structure.

Implantable device 110 may have two or more wires. In some embodiments, at least one wire is the reference portion, as defined hereinabove. In some embodiments, at least one wire may undergo biodegradation upon a defined physiological condition.

In some embodiments, the term "biodegradation" is used to denote hydrolytic, enzymatic and other metabolism-induced decomposition processes in the living organism, which result in a gradual dissolution of at least large parts of the implant.

Implantable device 110 may be fixedly attachable to the outer surface 104 of the tissue portions 103A and 103B such to cover, at least partially, or fully, reconnection site 102 using, for example, various fixation elements, e.g., glue, adhesives and/or sutures.

Implantable device 110 may have the form of a mesh-structure.

The term "mesh", as used herein, may refer to a two- or multidimensional semi-permeable structure of closely-spaced holes, which is composed of a plurality of elongated and interconnected elements, such as fibers, strands, struts, spokes, rungs made of a flexible/ductile material, which are arranged in an ordered (matrix, circular, spiral) or random fashion to form e.g., a two-dimensional sheet or a three-dimensional object.

In some embodiments, by "closely-spaced holes" it is meant to refer to a spacing of e.g., 1 mm, 2 mm, 5 mm, 10 mm, 15, mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, or 200 mm, including any value and range therebetween.

According to some embodiments, certain meshes may be composed of fibrous elements which come in direct physical contact with each other at each intercrossing junction constituting the mesh.

In some embodiments, the mesh structure comprises or is made of conductive, biocompatible and/or biodegradable material(s) as described hereinthroughout.

In some embodiments, the mesh or the wire structure comprises a core structure coated with conductive, biocompatible and/or biodegradable material(s) as described hereinthroughout.

In some embodiments, the core comprises one or more metals.

In some embodiments, the mesh structure comprises non-conductive polymer fibers that are interwoven with conductive, biocompatible and/or biodegradable material(s) as described hereinthroughout.

In some embodiments, the wire (or the mesh) has a uniformly porous architecture so that the degradation can be progressed uniformly.

In some embodiments, the term "mesh" is intended to include an element having an openwork fabric or structure, and may include but is not limited to, an interconnected network of wire-like segments, a sheet of material having numerous apertures and/or portions of material removed, or the like. Accordingly, the term "mesh" may also refer to a matrix or a net structure. A wire-like segment may for example comprise monofilaments and/or braided fibers.

In some embodiments, the mesh has a dimension of 0.1 to 20 mm×0.1 to 20 mm, including any value and range therebetween.

The outer surface 104 refers to the tissue surface which is pointing outwardly from the cavity of organ 101. Conversely, the inner surface 105 refers to the tissue surface which defines the boundaries of the lumen of organ 101.

The expression "fully covering" reconnection site 102 as used herein may refer to a configuration in which implantable device 110 is installed such that matter eventually leaking from organ 101 through an opening at any position of reconnection site 102 will come into contact with one or more of the wire-like segments of implantable device 110 and cause a change in the electrical properties of implantable device 110. Such matter may include liquids, solids and/or matter that is in a solid-fluid two-phase state.

As described hereinthroughout, in an embodiment, implantable device 110 may comprise conductive, and/or biodegradable material(s). In the event of leakage, biodegradable material(s) may, according to an embodiment, degrade quickly enough and to an extent which allows the detection of leakage from organ 101, e.g., within 6 hours, 3 hours, 1 hour, 30 min, 15 min, 10 min, 5 min, 1 min, or 30 seconds, from the moment at which body matter starts to leak through reconnection site 102. Further, the material(s) of implantable device 110 may be functional to allow detection of leakage for a time period that spans over, e.g., about at least e.g., 1 week, 2 weeks, 3 weeks, 4 weeks, or 6 weeks, from the time implantable device 110 was set in operable position within the mammalian body.

According to an embodiment, biodegradable material(s) employed may fully degrade within mammalian body after a few weeks, 1 month, a few months or years (e.g., after 6 months, 1 year, or two years).

Details of example biodegradable material are outlined herein below. In an embodiment, electrical wiring and/or implantable device 110 may be removable through a "port" (not shown) having an inner end and an outer end and which is provided in the mammalian body. For example, implantable device 110 may have a collapsible and meshed structure which, when being forced against the inner end from outside the mammalian body, collapses to attain a wire-like structure allowing its removal through the port. The removal may be accomplished as in the extraction of suturing material.

In an embodiment, the diameter of port may be of a magnitude to prevent infections and may for example range from 100 µm to 1 mm or from 100 µm to 4 mm.

As a result of such environmental changes (e.g., changes to or in the vicinity of the biological tissue to which implantable device 110 may be attached), a change in the electrical properties of implantable device 110 may occur, which may be detected by leak monitoring device 120. For example, and without being limited thereto, a change (e.g., drop) in pH value and/or concentration of ionic species may be detected by measuring a corresponding change (e.g., decrease) in the impedance of implantable device 110. In some embodiments specific enzymes affect the polymeric mesh structure. In some embodiments, pH value and/or concentration of ionic species affect the biodegradable metal.

In some embodiments, the pH value, following the environmental change (e.g., leakage of body matter), varies within less than ±0.5. In some embodiments, the pH value, following the change, varies within less than ±0.5 for at least 30 min, at least 1 h, at least 5 h, or at least 10 h.

In an additional non-limiting example, the environmental change refers to pH decrease. In an additional non-limiting example, the environmental change refers to an enzymatic activity increase. In an additional non-limiting example, the environmental change refers to a cytokine activity increase. In an additional non-limiting example, the environmental change refers to one or more symptoms derived from an inflammatory response e.g., pH, enzymes, oxidative stress, free radicals etc.

In some embodiments, "activity increase" refers to the increase in concentration e.g., of the corresponding enzyme or cytokine.

In some embodiments, "activity increase" refers to the increase in concentration of at least 1%, 2%, 3%, 4%, 5%, 6%, 7%, 8%, 9%, 10%, 11%, 12%, 13%, 14%, 15%, 16%, 17%, 18%, 19%, or 20%, including any value and range therebetween.

Without being hound by any particular mechanism, these changes in activity may increase the rate of wire or mesh degradation specifically at the organ site, and therefore may affect the electrical resistance of the wire or the mesh.

In some embodiments, the mesh or the wire structure comprises 2, 3, or 4 types of biodegradable conductive polymers and/or metals. Herein, by "type" it is meant to refer to a sensitivity property (e.g., degradability) of the polymer or the metal to a specific environmental change, e.g., an inflammatory disease or condition.

In some embodiments, by "inflammatory disease or condition" it is meant to refer to a local range of concentration of a specific enzyme or cytokine. In some embodiments, by "inflammatory disease or condition" it is meant to refer to a local range of concentration of a combination of factors, e.g., enzymes, cytokines, acidity etc.

In some embodiments, the term "cytokine" refers to a pro-inflammatory cytokine.

Non-limiting exemplary pro-inflammatory cytokines are selected from IL-1I, IL-3, IL-6, IL-12, p70, IL-17, MIP-1I and RANTES.

As already outlined herein, surgical site monitoring system 100 may further include leak monitoring device 120. According to some embodiments, leak monitoring device 120 may include a processor 121, a memory 122, an input device 123, an output device 124, and a power source 125 for powering the various components of leakage detector system 100.

The various components of surgical site monitoring system 100 may communicate with each other over one or more communication buses (not shown) and/or signal lines and/or communication links (not shown).

Leak monitoring device 120 may be operatively coupled with implantable device 110 so that changes of electrical properties of implantable device 110 are measurable by leak monitoring device 120, as outlined herein below in greater detail.

Leak monitoring device 120 may be operative to enable the implementation of a method, process and/or operation for allowing the detection of leakage from the lumen of organ 101 through a wall to the outside of the tract. Such method, process and/or operation may herein be implemented by a "detector engine" of leak monitoring device 120, referenced by alphanumeric label "126". Detector engine 126 may be realized by one or more hardware, software and/or hybrid hardware/software modules, e.g., as outlined herein. A module may be a self-contained hardware and/or software component that interfaces with a larger system (Alan Freedman, The Computer Glossary 268, ($8^{th}$ ed. 1998)) and may comprise a machine or machines executable instructions.

For example, a module may be implemented as a controller programmed to, or a hardware circuit comprising, e.g., custom VLSI circuits or gate arrays, off-the-shelf semiconductors such as logic chips, transistors, or other discrete components, configured to cause system 100 to implement the method, process and/or operation as disclosed herein. A module may also be implemented in programmable hardware devices such as field programmable gate arrays, programmable array logic, programmable logic devices or the like. For example, memory 122, may include instruction which, when executed e.g. by the processor 121, may cause the execution of the method, process and/or operation for enabling the detection of leakage from tract 101. Such method, process and/or operation may herein be implemented by leak detector engine 126.

According to some embodiments, an input device 123 of a leak monitoring device 120 may for example be operatively coupled with implantable device 110 e.g., through a plurality of electric wires (e.g., wires 111A and 111B). The plurality of electric wires may be removable from the mammalian body through the port and, as such, may be made or include non-biodegradable conductive material.

Wires or electrical wiring 111A and 111B may be coupled to implantable device 110 so that a sufficiently significant change in the material properties of implantable device 110 causes a change in an electrical property of the implant measurable by detector engine 126. A detection of a change in the electrical property of implantable device 110 may be conveyed to a user (not shown) via output device 124. In some embodiments, detector engine 126 may be configured to cause output device 124 to display values (e.g., auditory and/or visually) of the electrical properties as a function of time, e.g., within a calibrated scale.

In some embodiments, power source 125 may provide electrical energy to implantable device 110 for measuring changes of the device's electrical properties so that the magnitudes of electrical energy in the mammalian body are within physiologically tolerable values. A physiologically tolerable value may be, for example, an alternating current of 800 µA at a frequency of 50 kHz.

In some embodiments, input device 123 may be equipped with a transmitter (not shown) or a transmitter-receiver (transceiver), e.g., for allowing the transmission of signals carrying data ("electric-property-data") that is descriptive of a change of the electrical properties of implantable device 110 from input device 123 to a communication module (not shown) of leak monitoring device 120.

It is noted that in some embodiments, one or more components of leak monitoring device 120 may be internal and one or more components may be external to the mammalian body.

For example, input device 123 may be coupled with or include a transmitter (not shown) that may be operably positionable within mammalian body. Electric-property-data may be transmitted to outside mammalian body wirelessly over a communication link (not shown) to the communication module (not shown) of leak monitoring device 120 for further processing.

Leak monitoring device 120 may include a multifunction mobile communication device also known as "smartphone", a personal computer, a laptop computer, a tablet computer, a server (which may relate to one or more servers or storage systems and/or services associated with a business or corporate entity, including for example, a file hosting service, cloud storage service, online file storage provider, peer-to-peer file storage or hosting service and/or a cyberlocker), personal digital assistant, a workstation, a wearable device, a handheld computer, a notebook computer, a vehicular device, a stationary device and/or a home appliances control system.

The term "processor" as used herein may additionally or alternatively refer to a controller. Such processor may relate to various types of processors and/or processor architectures including, for example, embedded processors, communication processors, graphics processing unit (GPU)-accelerated computing, soft-core processors and/or embedded processors.

According to some embodiments, memory 122 may include one or more types of computer-readable storage media. Memory 122 may include transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache or flash memory. As working memory, memory 122 may, for example, process temporally-based instructions. As long-term memory, memory 122 may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, and the like.

A communication module may for example include I/O device drivers (not shown) and network interface drivers (not shown). A device driver may for example, interface with a keypad or to a USB port. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2 G, 3 G, 3.5 G, 4 G including for example Mobile WIMAX or Long Term Evolution (LTE) advanced, and/or any other current or future communication network, standard, and/or system.

Figure 2B:
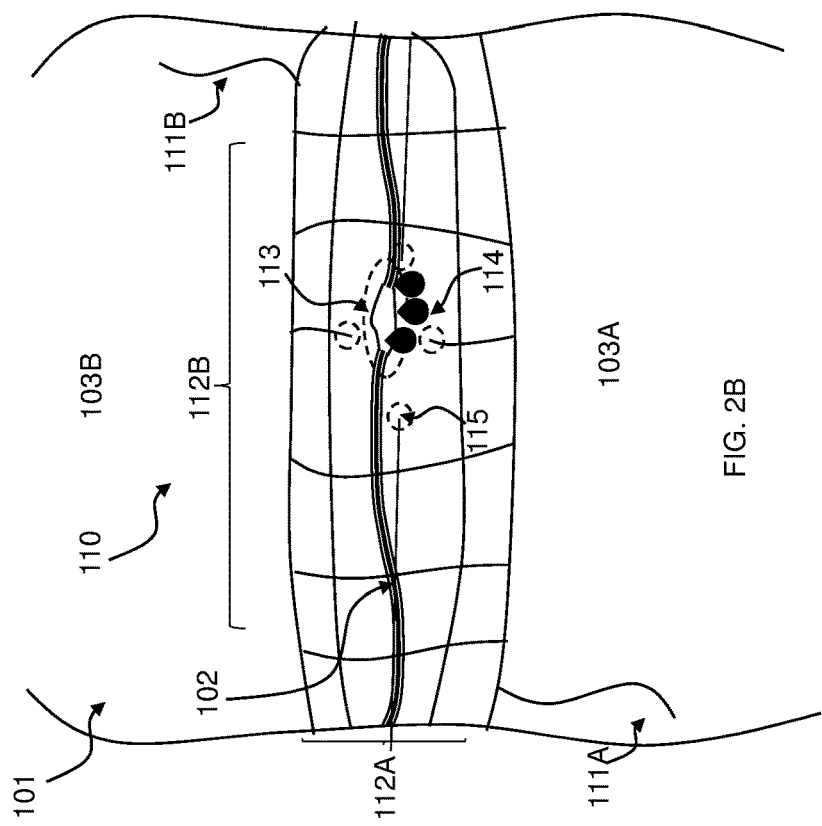
FIG. 2B schematically illustrates the implantable device of FIG. 2A where the implantable device's physical properties has undergone changes due to leakage of body matter from the organ, according to an embodiment.
Figure 2A:
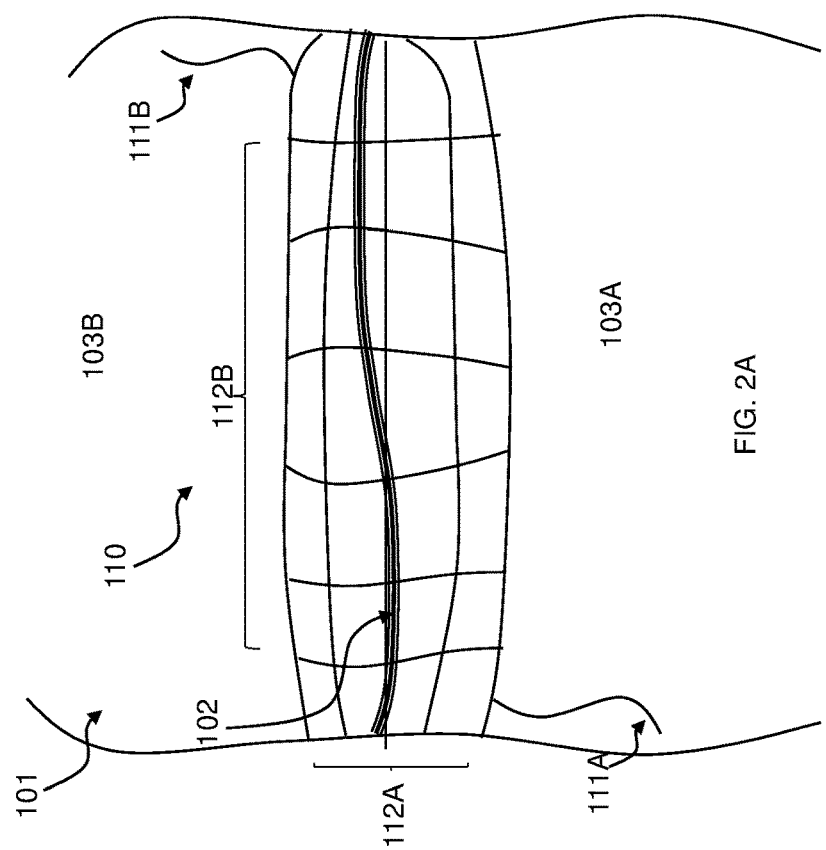
FIG. 2A schematically illustrates a plan view illustration of an implantable device of the system in an operable position adjunct to a tissue reconnection site of the GI tract.

Additional reference is made to FIGS. 2A and 2B. In some embodiments, implantable device 110 may have, as already indicated herein, a mesh structure or body. The mesh structure may, for example, comprise an interconnected network of wire-like segments 112A and 112B arranged (e.g., perpendicularly) relative to each other, to form a pattern of polygons delineating voids in the structure.

Referring to FIG. 2A, the mesh structure of implantable device 110 is shown to be intact, indicative that there is no leakage from the lumen of organ 101 through reconnection site 102 which connects between tissue portions 103A and 103B. When intact, implantable device 110 may have known electrical properties such as, for example, electric conductivity. As shown schematically in FIG. 2B, a section 113 of reconnection site 102 is shown to be reopened, allowing the leakage of matter 114 from the lumen of organ 101. As a result of the leakage of matter 114, mesh-structure of implantable device may undergo structural changes (e.g., partial or full degradation) in the vicinity of section 113. The structural change is schematically illustrated by loose ends 115 of previously continuous wire-like segments 112A and 112B of implantable device 110 and indicated at by dashed circles. Due to the structural changes of the mesh, the electrical properties of implantable device 110 or one of the mesh structure within implantable device 110 may change. Such change in the electrical properties of implantable device 110 (e.g., decrease in impedance) may be measurable by leakage engine 126. With respect to such indirect measurement, electrical impedance may increase if the material degrades, or even tears or breaks. However, with respect to direct measurement, electrical impedance may drop responsive to a decrease in pH for example.

According to an embodiment, examples of materials or composition of materials of which implantable device 110 may be made of or may comprise biodegradable conductive polymers and/or metals; biodegradable conductive polymers and/or metal in combination with and/or next to biodegradable and/or non-biodegradable non-conductive polymers. In an embodiment, the non-biodegradable residues of implantable device 110 may be removed through the port (not shown) of the mammalian body.

A combination of the employment of conductive and non-conductive materials may allow obtaining implantable devices 110 having respectively varying electrical properties. An implantable device 110 that is intact may for example exhibit an impedance ranging, e.g., up to $10^2$–$7.5 \times 10^3$ (S cm$^{-1}$).

A combination of biodegradable with non-biodegradable material may allow the control of the degradation products at the implantation site.

For example, as described hereinabove, change in the electrical properties of the biodegradable mesh structure within implantable device 110 may be measured with respect to a non-biodegradable wire- or mesh structure which is also positioned within implantable device 110.

For example, as described hereinabove, change in the electrical properties of the conductive mesh structure within implantable device 110 may be measured with respect to a non-conductive structure.

The material or composition of materials of which implantable device 110 may be made of may be non-toxic, e.g., to allow for it or their degradation products to be adsorbed by blood and/or cells of the mammalian body. Otherwise stated, material(s) of implantable device 110 may exhibit biocompatibility. More specifically, both material(s) of implantable device 110 may be biocompatible, as well as the degradation products may be biocompatible.

Biodegradable Conductive Polymers:

Non-limiting exemplary polymers for use with the biodegradable conducting polymer of the present invention include but are not limited to synthetic polymers such as poly (ethylene glycol), Polyglycolic acid (PGA) poly (ethylene oxide), partially or fully hydrolyzed poly(vinyl alcohol), polythiophene poly(vinylpyrrolidone), poly(ethyloxazoline), poly(ethylene oxide)-co-poly(propylene oxide) block copolymers, (polpxamers and meroxapols), poloxamines, oxyacetylene, polyparaphenylene, polyparaphenylene sulfide, polyaniline, polyisothionaphthene, polyparavinylene, carboxymethyl cellulose, and hydroxyalkylated celluloses such as hydroxyethyl cellulose and methylhydroxypropyl cellulose, and natural polymers such as polypeptides, polysaccharides or carbohydrates, hyaluronic acid, dextran, heparan sulfate, chondroitin sulfate, heparin, or alginate, and proteins such as gelatin, collagen, albumin, ovalbumin or any copolymers or blends thereof.

An example of a conductive polymer that may exhibit desired in-vitro and in-vivo biocompatibility includes the conjugated polymer Polypyrrole (PPy) and/or any derivatives thereof. PPy further exhibits relatively high conductivity under the desired physiological conditions ranging, for example, from 100 to 7,500 S/cm. PPy can be fabricated with high surface area such as fibers. The primary molecular structure of PPy is shown below:

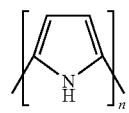

Examples of secondary molecular structures of PPy are shown below, wherein a plane array of the monomers are predominantly bound by α, α' bonds and to a lesser extent by α, β'; and β,β' bonds:

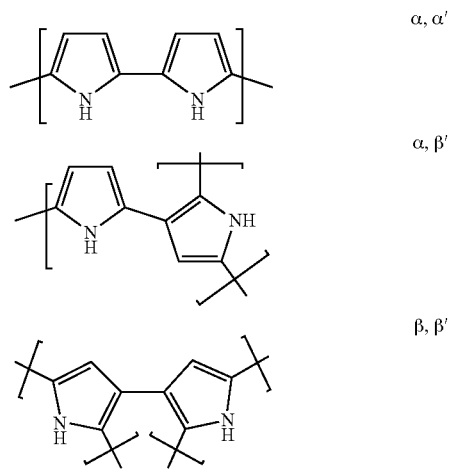

In an embodiment, conductive polymers such PPy can be synthesized to form a composite together with a biodegradable polymer. For example, PPy may be synthesized together with a biodegradable polymer to arrive at erodible PPy nanoparticle-polylactide (PLA), or PPy-PLLA composites. After biodegradation of the biodegradable polymer, non-degraded material may be removed from the mammalian body, e.g., through the port (not shown). The electrical properties and rate of degradation of the degradable polymer may be designed by selecting a corresponding ratio between the two polymers.

In an embodiment, the conductive polymer may be modified, e.g., by adding ionizable (butyric acid) and/or hydrolysable (butyric ester) side groups to the backbone of PPy.

In an embodiment, small chains of PPy that can undergo gradual erosion and renal clearance due to their small size may be electrochemically synthesized.

Biodegradable conductive metals:

In an embodiment, the conductive metal is selected from, without being limited thereto, Magnesium (Mg), Palladium (Pd), and Iron (Fe).

In an embodiment, magnesium may be employed by implantable device 110 for exhibiting suitable thrombogenicity and biocompatibility.

In some embodiments, the term "conductive metal" further refers to alloy e.g., Magnesium based alloy such as LAE442 and AZ91D. In some embodiments, the alloy may further comprise one or more elements selected from, without limitation, zirconium, yttrium, and an earth element.

In some embodiments, the magnesium alloy further comprises calcium (Ca). In some embodiments, the magnesium alloy further comprises zinc (Zn). In some embodiments, the magnesium alloy further comprises manganese. In some embodiments, the magnesium alloy further comprises tin. In some embodiments, the magnesium alloy is in the form of rod or wire.

In some embodiments, the term "magnesium" refers to magnesium hydroxide. In some embodiments, the conductive metal is stable at a desired pH range.

In an embodiment, a biodegradable material may be iron, e.g, Fe>99.8%. Iron can interconvert between ferric ($Fe^{2+}$) and ferrous ($Fe^{3+}$) ions by accepting and donating electrons quite readily, which makes it a useful component for cytochromes, oxygen-binding molecules (e.g., hemoglobin and myoglobin), and/or enzymes.

In another embodiment, the metal (or the alloy) is at least partially coated by a protective layer. In some embodiments, the protective layer comprises one or more non-metallic derivatives.

Biodegradable non-conductive polymers in conjunction with biodegradable conductive metal:

In an embodiment, a mesh structure of implantable device 110 may employ biocompatible, biodegradable, and/or non-conductive polymer fibers that are interwoven with biodegradable conductive metals.

Biodegradable implantable device 110 or a portion thereof can be degraded with time at a known, pre-designed rate until the completion of the healing process, thus, for example, circumventing the need to perform unnecessary surgical procedures to remove the supporting implant and significantly reduce the risks and costs involved.

The biodegradable polymer mesh (materials such as, for example, PGA and/or PLA) may have a profile of, e.g., 100 μm-1 mm in diameter, while the metal fibers may have a profile ranging, for example, from 5 to 20 μm or 5 to 500 μm.

Non-biodegradable, non-conductive polymers in conjunction with biodegradable conductive metal:

In an embodiment, a mesh structure of implantable device 110 may employ biocompatible, non-biodegradable, non-conductive polymer fibers such as, without limitation, nylon, polyethylene terephthalate (PET), ultra-high-molecular-weight polyethylene (UHMPE), etc., and may be interwoven with biodegradable conductive metal fibers. The non-biodegradable mesh polymer can serve as a mechanical carrier for the biodegradable conductive metal.

Figure 3:
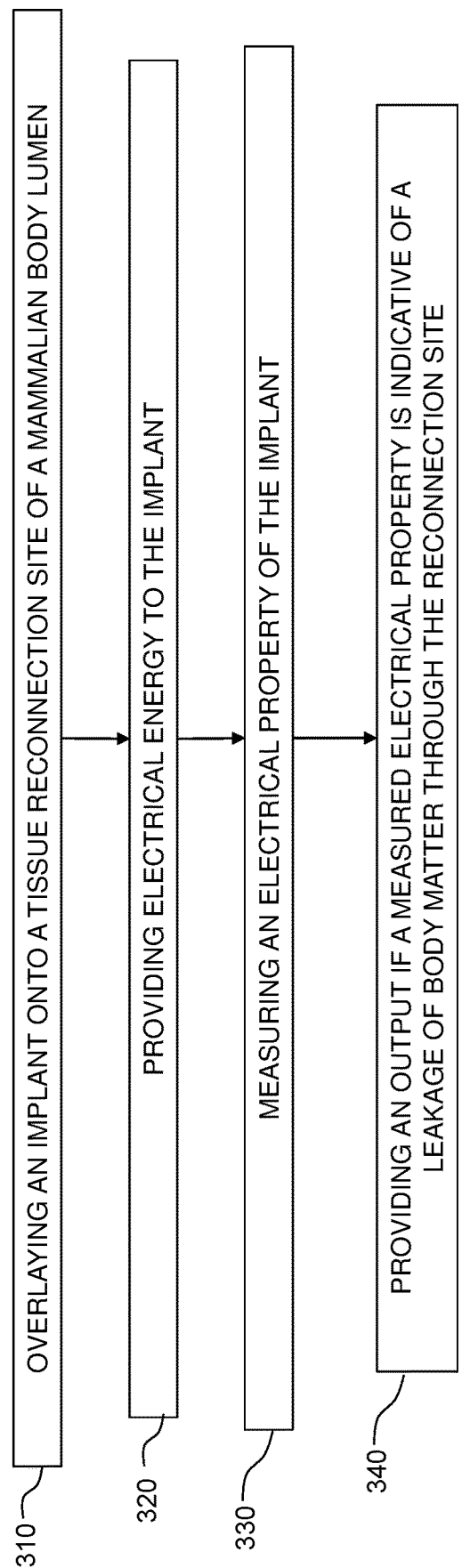
FIG. 3 is a flow chart illustration of a method for monitoring the integrity of an organ, according to an embodiment.

Further reference is made to FIG. 3. According to an embodiment, a method for detecting leakage of matter from a mammalian body organ may include, as indicated by box 310, overlaying implantable device 110 onto tissue reconnection site 102 of a mammalian body organ.

The method may further include, as indicated by box 320, providing electrical energy to implantable device 110.

The method may include, as indicated by box 330, measuring an electrical property of implantable device 110.

The method may further include, as indicated by box 340, providing an output if a measured electrical property is indicative of a leakage of matter through the reconnection site.

The various features and steps discussed above, as well as other known equivalents for each such feature or step, can be mixed and matched by one of ordinary skill in this art to perform methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein. For example, any digital computer system can be configured or otherwise programmed to implement a method disclosed herein, and to the extent that a particular digital computer system is configured to implement such a method, it is within the scope and spirit of the disclosure. Once a digital computer system is programmed to perform particular functions pursuant to computer-executable instructions from program software that implements a method disclosed herein, it in effect becomes a special purpose computer particular to an embodiment of the method disclosed herein. The techniques necessary to achieve this are well known to those skilled in the art and thus are not further described herein. The methods and/or processes disclosed herein may be implemented as a computer program product such as, for example, a computer program tangibly embodied in an information carrier, for example, in a non-transitory computer-readable or non-transitory machine-readable storage device and/or in a propagated signal, for execution by or to control the operation of, a data processing apparatus including, for example, one or more programmable processors and/or one or more computers. The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by a communication network.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

"Coupled with" means indirectly or directly "coupled with".

Where applicable, although state diagrams, flow diagrams or both may be used to describe embodiments, the technique is not limited to those diagrams or to the corresponding descriptions. For example, flow need not move through each illustrated box or state, or in exactly the same order as illustrated and described.

It should be understood that where the claims or specification refer to "a" or "an" element, such reference is not to be construed as there being only one of that element.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made.

All references mentioned in this specification are herein incorporated in their entirety by reference into the specification, to the same extent as if each individual patent was specifically and individually indicated to be incorporated herein by reference. In addition, citation or identification of any reference in this application shall not be construed as an admission that such reference is available as prior art to the present application.

EXAMPLES

Reference is now made to the following examples, which together with the above descriptions illustrate some embodiments of the invention in a non-limiting fashion.

Example 1

General Procedure

Reference is now made to FIG. 4 which illustrates a colon as the surgical site 415A and a mesh 405A being implanted thereon.

In exemplary procedures, two meshes (detection electrode, and reference electrode) in a mesh density of 1 to 8 mm×1 to 8 mm and at least 2 mm×2 mm opening composed of wires (d=150 μm) are implanted, one (405A) at the surgical site (415A) and another (405B) at a different location of the colon (415B) further from the surgical site.

In exemplary procedures, potential or current are measured between surgical site, points 410, and/or 420 and references sites, 430, and/or 440 and are compared.

In exemplary procedures, an inflammatory response occurs owing to GI leakage that triggers inflammatory cascade which in turn provides high corrosive environment at the surgical site.

In exemplary procedures, the mesh at the surgical site degrades faster compared to the reference mesh electrode. The potential (or current) measured between points 410, 420 is higher compared to the potential (or current) measured between points 430, 440.

In exemplary procedures, the potential (or current) is measured right after surgery and 2, 3, 4 to 6 days post-surgery.

In additional exemplary procedures, the two electrodes are placed at the same site during surgery, whereas one electrode known to be less influenced by inflammatory response and its degradation would be relatively stable.

In exemplary procedures, an electrode known to be less influenced by inflammatory response is obtained by its coating thereof with slow (about a year) degradable polymer, or other type of metal/alloy.

In additional exemplary procedures alternating current (AC) electrochemical impedance is measured.

In additional exemplary procedures, the coating is 10-100 μm thickness.

In additional exemplary procedures, the coating is permeable to the electrolyte solution so as to allow current/potential measurement in relative to the specific body fluids.

Example 2

MMP-8 and MMP-9 Measurement by Direct Current Polarization Technique

General Concept:
In exemplary procedures, the levels of MMP-8 and -9 are measured.

In exemplary procedures, the levels are found to be significantly higher in patients who developed anastomotic leakage, as well as biopsies from patients with impaired anastomotic healing.

In exemplary procedures, the degradation (also referred to as "corrosion") model comprises an intermetallic particle, a magnesium anodic metal, and insulation. The particle plays the role of a cathode in micro-galvanic magnesium corrosion.

In exemplary procedures, magnesium ion concentration sharply increases on the boundary between the anodic and cathodic region as the pH in the solution decreases. This shows, without being bound by any particular theory, that magnesium tends to corrode rapidly in an acid solution as compared to a neutral or alkaline solution.

Materials
  Mg 99.9%
  AZ91 magnesium alloy
  Mg—Ca alloy
  ZX50 and WZ21 alloys
  Mg—Zn—Ca
  Iron (Fe>99.8%)
  Conductive polymers—polypyrrole (PPy), polyaniline (PANi), polythiophene.

Media
  Data exist in regards to trauma or inflammation that is responsible to enzymes released by cells, such as polymorpho-nuclear leucocytes and consequently increase rate of degradation in the polymer.

In exemplary embodiments, the control solution has pH 7 and does not contain enzymes.

In exemplary procedures the test solution comprises 0.1 M NaCl (pH 6).

In additional exemplary embodiments, the test/control solution comprise phosphate buffered saline (PBS) solution.

In additional exemplary embodiments, the test solution contains MMP-1, MMP-2, MMP-8 and MMP-9 in the medium.

Method
In exemplary procedures, during direct current polarization (DCP) test the voltage is swept at a controlled rate (1 mVs$^{-1}$) between different pre-set potentials by regulating the current flowing between the working (Mg) and counter (inert metal) electrode.

In exemplary procedures, open circuit potential (OCP) is recorded before DCP for a set period of exposure time that allows the material to "stabilize" with the electrolyte and reach a near steady potential. The DCP initial voltage is nominally set to commence at values more negative than (i.e. cathodic to) the OCP, and the scan proceeds to increasingly positive values (that are anodic to the original OCP).

In exemplary procedures, the DCP results show as a Tafel curve, which provides thermodynamic information on corrosion potential ($E_{corr}$), kinetic information from the corrosion current density ($i_{corr}$) as well as relative anodic and cathodic reactions.

Results
In exemplary procedures, the measured $E_{corr}$ is between −1V to 1.6V and in the control solution and $E_{corr}$ of ~−1.7V and −2V in test solution.

In exemplary procedures, the measured $i_{corr}$ in the control solution is between 2 to 10 μA/cm$^2$) and in the test solution $i_{corr}$ is (20 to 30 μA/cm$^2$).

Example 3

Electrochemical Impedance Spectroscopeis

Method

In exemplary procedures, an electrochemical impedance spectroscopy (EIS) technique is used to characterize a magnesium sample using the frequency response of AC polarization of pure magnesium (99.9%) substrate.

EIS uses a range of low magnitude polarizing voltages that cycle from a peak anodic to peak cathodic voltage using a spectra of voltage frequencies. Capacitance and resistance values are obtained for each frequency and can then be used to illuminate a number of phenomena and properties of the Mg surface.

Results

In exemplary procedures, the impedance in the control solution (see Example 2) is between 20 and 100 ohm·cm$^2$ compared to an impedance of between 1 and 15 at the test solution (see Example 2). This occurs in more than 50% of the frequency range measured between 10-2 Hz and 105 Hz.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An implantable device for detecting leakage of body matter from an organ comprising:
   a controller,
   at least two wires operatively connected to the controller,
   wherein at least one wire of the at least two wires is configured to attach along a site of the organ, and wherein the at least one wire comprises a biodegradable conductive polymer and/or a biodegradable conductive metal;
   wherein the at least one wire of the at least two wires, when configured to be subjected to or engaged with the body matter, is configured to undergo structural changes including at least partial material degradation; and
   wherein the controller is configured to detect leakage of the body matter from the organ, based on detection of the structural changes of the at least one wire.

2. The implantable device of claim 1, wherein the controller is configured to monitor biological tissue leakage of the body matter from the organ by detecting leakage of the body matter from the organ based on the structural changes of the at least one wire.

3. The implantable device of claim 1, wherein said at least two wires are in a form of mesh structure.

4. The implantable device of claim 1, wherein at least one wire of the at least two wires is configured to be positioned external to the site of a body organ.

5. The implantable device of claim 1, wherein said biodegradable conductive metal comprises a metal selected from a group consisting of magnesium, iron, zinc and calcium, or any combination thereof.

6. The implantable device of claim 1, wherein said organ is an esophagus, stomach, small intestine, or large intestine.

7. The implantable device of claim 1, wherein said biodegradable conductive polymer or said biodegradable conductive metal is characterized as being measurably responsive in terms of an electrical conductivity of said biodegradable conductive polymer or said biodegradable conductive metal when being subjected to the body matter leaking from the organ.

8. The implantable device of claim 7, wherein said body matter is a cytokine or an enzyme.

9. The implantable device of claim 8 wherein said enzyme is metalloproteinase.

10. The implantable device of claim 9 wherein said metalloproteinase is selected from a group consisting of matrix metalloproteinase (MMP)-8 and MMP-9, or a combination thereof.

11. The implantable device of claim 1, wherein said biodegradable conductive polymer or said biodegradable conductive metal is characterized by a conductivity of 100 to 7,500 S/cm.

12. The implantable device of claim 1, wherein at least one of the at least two wires comprises a reference portion from which structural changes can be measured and/or calculated.

13. A system for monitoring a site within a mammalian body, comprising:
    an implantable device configured to be operably attachable to an organ inside the mammalian body; and comprising:
    at least two wires:
    wherein at least one wire of the at least two wires is configured to attach along a site of the organ, and wherein the at least one wire comprises a conductive polymer and/or a conductive metal,
    wherein the at least one wire of the at least two wires, when configured to be subjected to or engaged with body matter, is configured to undergo structural changes, and
    the system further comprising a leak monitoring device for monitoring leakage of the body matter from the organ, the leak monitoring device being operably coupled with the implantable device and which comprises:
    a power source configured to supply electrical energy to the implantable device; and
    a detector engine configured to detect the structural changes in the at least one wire resulting from the leakage of the body matter from the organ by measuring changes in electrical properties of the implantable device.

14. A method comprising:
    attaching at least one wire along a site of an organ, wherein the at least one wire comprises a biodegradable conductive polymer and/or a biodegradable conductive metal,
    wherein at least one of the at least two wires, when being subjected to or engaging with body matter, is configured to undergo structural changes including at least partial material degradation; and
    monitoring biological tissue leakage of the body matter from the organ, wherein the monitoring comprises performing, by at least one memory storing executable instructions, and at least one processor executing the executable instructions:

detecting leakage of the body matter from the organ based on detection of structural changes of the at least one wire.

15. The method of claim 14, wherein said organ an esophagus, stomach, small intestine, or large intestine.

16. The method of claim 14, further comprising attaching at least one second wire positioned external to the site of the organ.

17. The method of claim 14, wherein said biodegradable conductive polymer or said biodegradable conductive metal is characterized by a conductivity of 100 to 7,500 S/cm.

18. The method of claim 14 wherein said body matter is a cytokine or an enzyme.

19. The method of claim 18, wherein said enzyme is metalloproteinase.

20. The method of claim 19, wherein said metalloproteinase is selected from a group consisting of MMP-8 and MMP-9, or a combination thereof.

* * * * *